(12) United States Patent
Chen et al.

(10) Patent No.: US 7,176,350 B2
(45) Date of Patent: Feb. 13, 2007

(54) METHOD FOR CONTROLLING RATIO OF PROTEINS/LIPIDS IN CROP SEEDS

(75) Inventors: Jinqing Chen, Zhejiang Hangzhou (CN); Chunxiu Lang, Zhejiang Hangzhou (CN); Ruizhi Huang, Zhejiang Hangzhou (CN); Zhanghu Hu, Zhejiang Hangzhou (CN); Xhihong Liu, Zhejiang Hangzhou (CN)

(73) Assignee: Zhejiang Academy of Agricultural Science, Zhejiang Hangzhou (CN)

( * ) Notice: Subject to any disclaimer, the term of this patent is extended or adjusted under 35 U.S.C. 154(b) by 426 days.

(21) Appl. No.: 10/142,111

(22) Filed: May 8, 2002

(65) Prior Publication Data
US 2003/0101485 A1    May 29, 2003

Related U.S. Application Data

(63) Continuation of application No. PCT/CN00/00418, filed on Nov. 6, 2000.

(30) Foreign Application Priority Data
Nov. 9, 1999    (CN) ............................. 99124511.3

(51) Int. Cl.
*C12N 15/82*    (2006.01)

(52) U.S. Cl. ..................... 800/281; 800/298

(58) Field of Classification Search ................ 800/281, 800/298; 435/419, 468
See application file for complete search history.

(56) References Cited

U.S. PATENT DOCUMENTS

| 5,530,192 A | 6/1996 | Murase et al. ............ 800/205 |
| 5,914,449 A * | 6/1999 | Murase et al. ............ 800/281 |

FOREIGN PATENT DOCUMENTS

| JP | 95-143887 | 6/1995 |
| WO | WO 92/04456 | 3/1992 |

OTHER PUBLICATIONS

Gehlen et al, Plant Molecular Biology 32: 831-848, 1996.*
Sugimoto, Toshio, et al. "Phosphoenolpyruvate Carboxylase Level in Soybean Seed Highly Correlates to its Contents of Protein and Lipid", *Agri. Biol. Chem.*, 53 (3); pp. 885-887 (1989).

\* cited by examiner

*Primary Examiner*—Elizabeth F. McElwain
(74) *Attorney, Agent, or Firm*—Dorsey & Whitney LLP

(57) ABSTRACT

A method for altering the ratio of proteins/lipids in crop seeds utilizing the antisense gene, comprising the steps of: (1) cloning the gene for the phosphoenopyruvate carboxylase or acetyl-CoA carboxylase, or the fragment thereof; (2) constructing the corresponding antigene; (3) introducing the said antigene into the cells of the rapeseeds, so that the activity of the phosphoenopyruvate carboxylase or the acetyl-CoA carboxylase being important for the protein synthesis is changed, the flow direction of the common substrate, PEP, can be controlled, so that the proteins/lipids in the seeds is altered. The application can be used to alter the proteins/lipids in the crop seeds.

9 Claims, 6 Drawing Sheets

SEQUENCE LISTING

```
<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<221> NAME/KEY: misc_feature
<223> OTHER INFORMATION: primer

<400> SEQUENCE: 1
ggaatctaaa gtaaaccggc                                                      20

<210> SEQ ID NO 2
<211> LENGTH: 20
<212> TYPE: DNA
<213> ORGANISM: Artificial Sequence
<220> FEATURE:
<221> NAME/KEY: misc_feature
<223> OTHER INFORMATION: primer

<400> SEQUENCE: 2
ctctctgaat ccttctgtag                                                      20

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: primer

<400> SEQUENCE: 3
aaccgacggc cgtgactgta                                                      20

<210> SEQ ID NO 4
<211> LENGTH: 20
<212> TYPE: DNA
<213> ORGANISM: Artificial Sequence
<220> FEATURE:
<221> NAME/KEY: misc_feature
<223> OTHER INFORMATION: primer

<400> SEQUENCE: 4
cgtaagggat gacgcacaat                                                      20

<210> SEQ ID NO 5
<211> LENGTH: 18
<212> TYPE: DNA
<213> ORGANISM: Artificial Sequence
<220> FEATURE:
<221> NAME/KEY: misc_feature
<223> OTHER INFORMATION: primer

<400> SEQUENCE: 5
cgcaagaccg gcaacagg                                                        18

<210> SEQ ID NO 6
<211> LENGTH: 10
<212> TYPE: DNA
<213> ORGANISM: Artificial Sequence
<220> FEATURE:
<221> NAME/KEY: misc_feature
<223> OTHER INFORMATION: primer
```

```
<400> SEQUENCE: 6
gtttcgctcc                                                              10

<210> SEQ ID NO 7
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 7
tgatccctgg                                                              10

<210> SEQ ID NO 8
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 8
catcccctg                                                               10

<210> SEQ ID NO 9
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 9
ggactggagt                                                              10

<210> SEQ ID NO 10
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 10
tgcgcccttc                                                              10

<210> SEQ ID NO 11
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 11
tgctctgccc                                                              10

<210> SEQ ID NO 12
<211> LENGTH: 10
<212> TYPE: DNA
<213> ORGANISM: Artificial Sequence
<220> FEATURE:
<221> NAME/KEY: misc_feature
<223> OTHER INFORMATION: primer
```

```
<400> SEQUENCE: 12
ggtgacgcag                                                          10

<210> SEQ ID NO 13
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 13
gtccacacgg                                                          10

<210> SEQ ID NO 14
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 14
tgggggactc                                                          10

<210> SEQ ID NO 15
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 15
ctgctgggac                                                          10

<210> SEQ ID NO 16
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 16
gtagacccgt                                                          10

<210> SEQ ID NO 17
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 17
ccttgacgca                                                          10

<210> SEQ ID NO 18
<211> LENGTH: 10
<212> TYPE: DNA
<213> ORGANISM: Artificial Sequence
<220> FEATURE:
<221> NAME/KEY: misc_feature
<223> OTHER INFORMATION: primer
```

```
<400> SEQUENCE: 18
ttcccccgct                                                          10

<210> SEQ ID NO 19
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 19
tccgctctgg                                                          10

<210> SEQ ID NO 20
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 20
ggagggtgtt                                                          10

<210> SEQ ID NO 21
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 21
tttgcccgga                                                          10

<210> SEQ ID NO 22
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 22
agggaacgag                                                          10

<210> SEQ ID NO 23
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 23
ccacagcagt                                                          10

<210> SEQ ID NO 24
<211> LENGTH: 10
<212> TYPE: DNA
<213> ORGANISM: Artificial Sequence
<220> FEATURE:
<221> NAME/KEY: misc_feature
<223> OTHER INFORMATION: primer
```

```
<400> SEQUENCE: 24 accccccgaag                                                             10

<210> SEQ ID NO 25
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 25
ggacccttac                                                              10

<210> SEQ ID NO 26
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 26
caggcccttc                                                              10

<210> SEQ ID NO 27
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 27
tgccgagctg                                                              10

<210> SEQ ID NO 28
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 28
agtcagccac                                                              10

<210> SEQ ID NO 29
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 29
aatcgggctg                                                              10

<210> SEQ ID NO 30
<211> LENGTH: 10
<212> TYPE: DNA
<213> ORGANISM: Artificial Sequence
<220> FEATURE:
<221> NAME/KEY: misc_feature
<223> OTHER INFORMATION: primer
```

```
<400> SEQUENCE: 30
agggtcttg                                                           10

<210> SEQ ID NO 31
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 31
gtgacgtagg                                                          10

<210> SEQ ID NO 32
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 32
gggtaacgcc                                                          10

<210> SEQ ID NO 33
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 33
ggcactgagg                                                          10

<210> SEQ ID NO 34
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 34
acgcatcgca                                                          10

<210> SEQ ID NO 35
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 35
acgcgcatgt                                                          10

<210> SEQ ID NO 36
<211> LENGTH: 10
<212> TYPE: DNA
<213> ORGANISM: Artificial Sequence
<220> FEATURE:
<221> NAME/KEY: misc_feature
<223> OTHER INFORMATION: primer
```

```
<400> SEQUENCE: 36
tgctgcaggt                                                            10

<210> SEQ ID NO 37
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 37
ttccccgcga                                                            10

<210> SEQ ID NO 38
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 38
ctgatgcgtg                                                            10

<210> SEQ ID NO 39
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 39
gggtctcggt                                                            10

<210> SEQ ID NO 40
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 40
gtctccgcaa                                                            10

<210> SEQ ID NO 41
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 41
gagggaagag                                                            10

<210> SEQ ID NO 42
<211> LENGTH: 10
<212> TYPE: DNA
<213> ORGANISM: Artificial Sequence
<220> FEATURE:
<221> NAME/KEY: misc_feature
<223> OTHER INFORMATION: primer
```

```
<400> SEQUENCE: 42
actgaacgcc                                                                10

<210> SEQ ID NO 43
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 43
ggtgctccgt                                                                10

<210> SEQ ID NO 44
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 44
gtggtccgca                                                                10

<210> SEQ ID NO 45
<211> LENGTH: 10
<212> TYPE: DNA
<213> ORGANISM: Artificial Sequence
<220> FEATURE:
<221> NAME/KEY: misc_feature
<223> OTHER INFORMATION: primer

<400> SEQUENCE: 45
gctaacgtcc                                                                10

<210> SEQ ID NO 46
<211> LENGTH: 29
<212> TYPE: DNA
<213> ORGANISM: Artificial Sequence
<220> FEATURE:
<221> NAME/KEY: misc_feature
<223> OTHER INFORMATION: primer

<400> SEQUENCE: 46
gwggwggsac wgtbggraga ggaggkccv                                           29
```

METHOD FOR CONTROLLING RATIO OF PROTEINS/LIPIDS IN CROP SEEDS

PRIORITY CLAIM

This application is a continuation of International Patent Application PCT/CN00/00418, filed on Nov. 6, 2000, which claims priority to an earlier filed Chinese Application Number CN 99124511.3, filed on Nov. 9, 1999.

BACKGROUND OF THE INVENTION

1. Field of the Invention

The present invention relates generally to the field of crop breeding. More specifically, the present invention relates to a method for controlling the ratio of proteins/lipids in crop seeds using antigenes, and new plants with high oil or protein productivity produced thereby.

2. Description of the Related Art

It has been known to increase the protein or lipid content in crop seeds via conventional breeding or positive genetic regulation. Typically, the conventional breeding can only increase the specific content in crop seeds by 2~3%, due to the limited genetic varieties in the sources. Specifically, the conventional breeding is carried out by selecting the desired properties among the mutants derived from random variations without being directed. The drawbacks of this method include randomness and the amount of time consumed in obtaining the genetic stability.

Positive sense genetic engineering can theoretically provide the possibility of directionally increasing the content of protein or lipid in crop seeds. However, being technically difficult to practice, it is far from the industrial application. In this connection, for example, the increment is limited, the expression patterns of the target genes in vivo are complex, and it is difficult to obtain the balance among the desired properties. Until now, there has been no success reported in this connection.

In the early 50's, it was found that the contents of proteins and lipids were inversely correlated to each other. Thereafter, in the 80's, it was found that, in soybeans, the protein content was positively related to the activity of the phosphoenopyruvate carboxylase (PEPCase)(Agri. Bio. Chem., 1989,53(3), ps. 885~887). Actually, the biosynthesis of either protein or lipid takes the phosphoenopyruvate as the common substrate. The phosphoenopyruvate is one of the products in glycolysis. It can either be converted into oxaloacetic acid by the PEPCase, or pyruvate, by the pyruvate kinase. The former directly participates in the anabolism of protein. On the other hand, the latter is first converted into acetyl-CoA by pyruvate dehydrogenase and then into Malonyl-CoA by the acetyl-CoA carboxylase (ACCase), and finally participates in the anabolism of fatty acid in this form. Therefore, it is indicated that the relative activity of PEPCase to ACCase, or vice versa, controls the flow direction of the common substrate, phosphoenopyruvate and the ratio of proteins/lipids produced.

Accordingly, it is an object of the present invention to provide a method for controlling the ratio of proteins/lipids in the crop seeds. The method of the invention is more practicable, time saving and genetically stable. Another object of the present invention is to provide new crops improved in the productivity of oil/protein by the method of the invention.

SUMMARY OF THE INVENTION

The present invention provides a method for controlling the ratio of proteins/lipids in the crop seeds, comprising the steps of:

(1) Cloning the gene for phosphoenolpyruvate carboxylase (PEPCase) or acetyl-coenzyme A carboxylase (ACCase), or a fragment thereof;
(2) Constructing the antigene as Anti-PEP or Anti-ACC from the clone of step (1);
(3) Transforming the said antgene into the desired plant cells.

In addition, the present invention provides new crops containing in their genome homozygous anti-PEP gene or anti-ACC gene. Optionally, a genetically stable line can be established via selection for 3–4 generations from the parents.

Other and further aspects, features and advantages of the present invention will be apparent from the following description of the preferred embodiment of the invention given for the purpose of disclosure.

FIG. a shows the PCR result: M: DNA Mark λ DNA/Hind III, lane 1: the PCR product of pPEPA5, lane 2: the PCR product of the non-transgenic plant as control; lane 3: the PCR product of transgenic plant.

FIG. b shows the Southern blot assay. Lane 1: DNA Mark λ DNA/Hind III, 2: the transgenic plant of the invention.

FIG. c shows the result of GUS assay. Lane 1: the transgenic plant of the invention, Lane 2: *non-transgenic control*.

Figure 6:
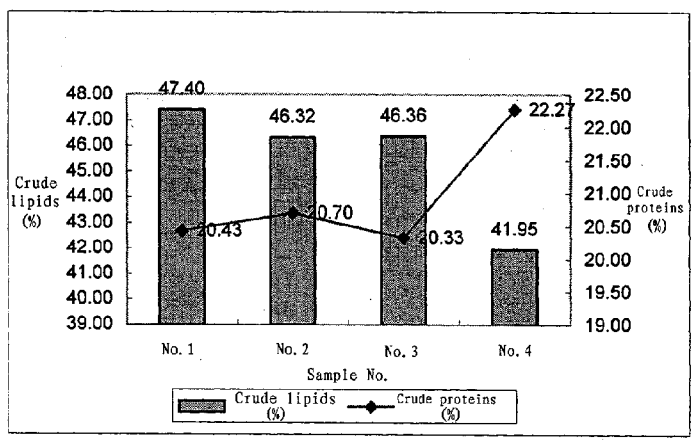

FIG. 6 shows the comparison of the contents of protein and lipid between the homozygous lines of Zheyou 758/Anti-PEP and the hybrid lines.

Figure 7:
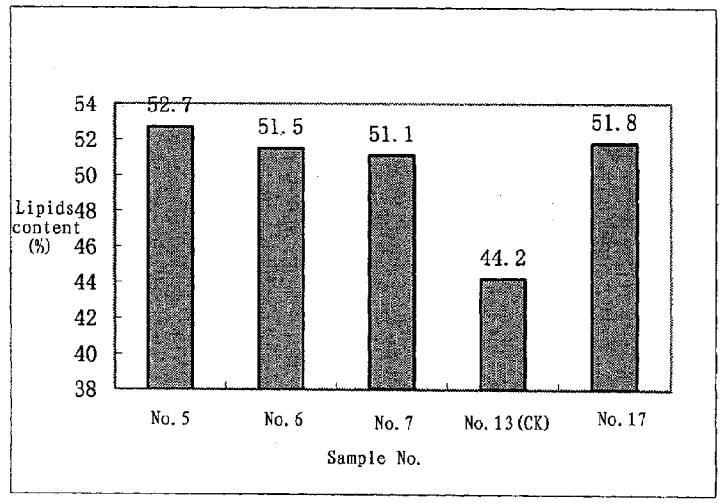

FIG. 7 shows the comparison of content of proteins with that of lipid in the plant of the T2 progeny of Zheyouyou No. 1/Anti-PEP.

Figure 8:
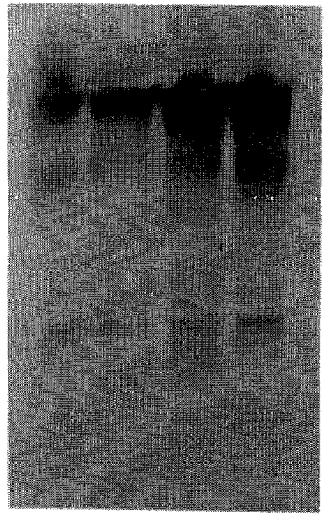

FIG. 8 shows the SDS-PAGE electrophoresis pattern, wherein, Lane 1: the non-transgenic control; Lane 2 to 4: the transgenic rapeseed plants of the invention.

Figure 9:
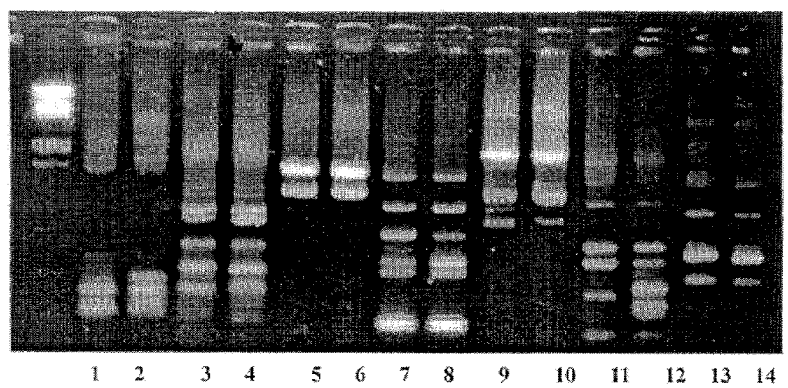

FIG. 9 shows the result of RAPD (Random Amplified Polymorphic DNA) analysis of the transgenic rapeseeds of the invention, indicating the difference of one primer. Lanes in odd numbers are non-transgenic Zheyouyou, those in even numbers are Zheyouyou No. 1/Anti-PEP.

Figure 10:
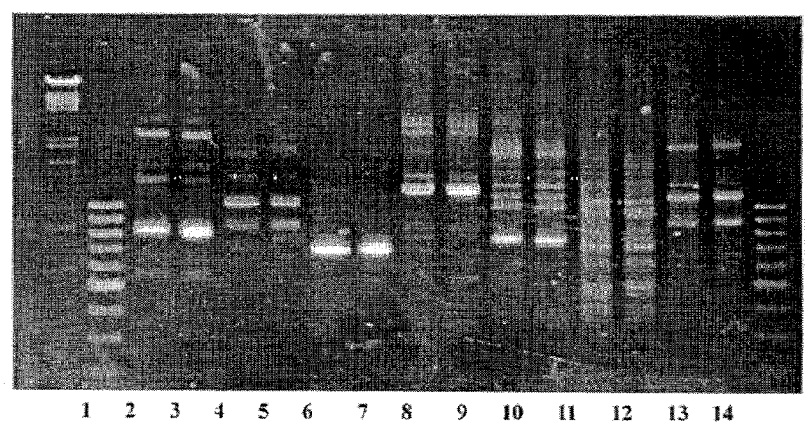

FIG. 10 shows the result of RAPD analysis of the transgenic rapeseeds of the invention, indicating the fair consistency in the two samples, wherein, Lanes in odd numbers are non-transgenic Zheyouyou, those in even numbers are Zheyouyou No. 1/Anti-PEP.

Figure 11:
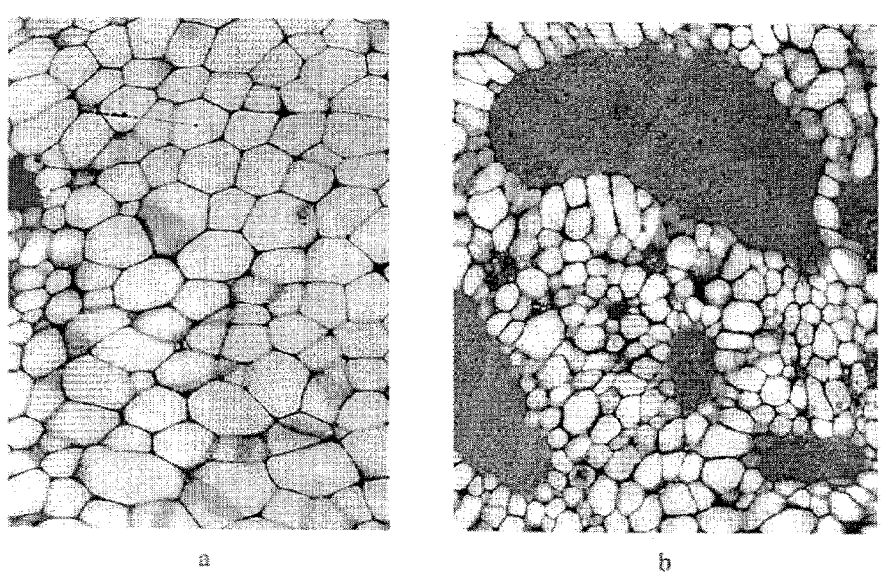

FIG. 11 shows the ultra-microscopic examination of the seeds of the transgenic rapeseed of the invention in comparison with that of the control (×1000).

FIG. a: Zheyouyou No. 1/Anti-PEP.

FIG. b: non-transgenic Zheyouyou No. 1.

Figure 12:
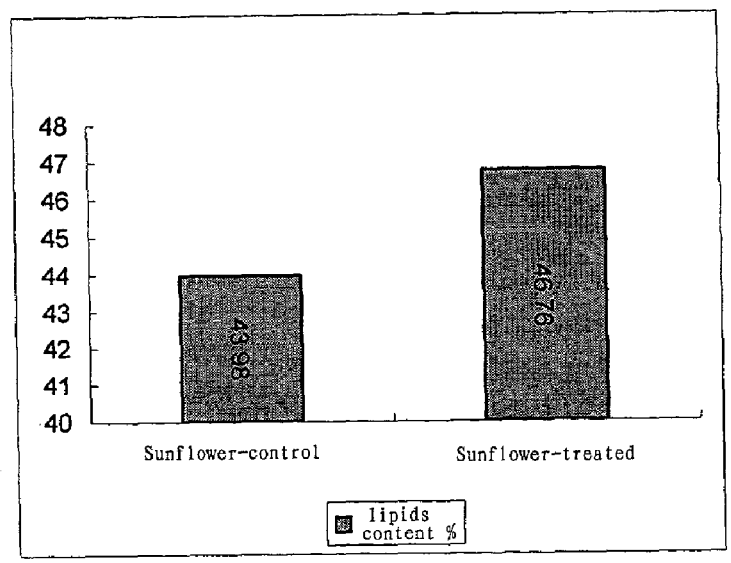

FIG. 12 shows the effects of the anti-PEP strategy in sunflower.

Figure 13:
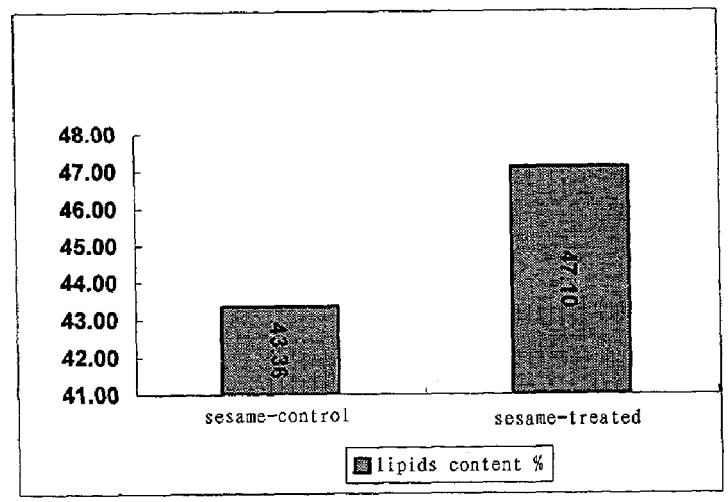

FIG. 13 shows the effects of the anti-PEP strategy in sesame.

DETAILED DESCRIPTION OF THE INVENTION

The object of the present invention to control the ratio of proteins/lipids in crop seeds was accomplished by means of controlling the flow direction of the phosphoenopyruvate, the common substrate of the biosyntheses of protein and lipid. For example, the anti-PEP gene was introduced into the plant cell to block the activity of PEPCase, which relatively increased the activity of ACCase, so that more PEP flowed in the direction to the lipid biosynthesis, and consequently increased the lipid content in the crop seeds. Similarly, introducing the anti-ACC gene will increase the proteins content.

All those protein or oil crops are suitable for the method of the invention, including but not limited to soybean, rapeseed, peanuts, sunflower, and sesame.

The method of the invention comprises at least the steps of: (1) Cloning the gene for phosphoenolpyruvate carboxylase (PEPCase) or acetyl-coenzyme A carboxylase (ACCase), or a fragment thereof; (2) Constructing the antigene as Anti-PEP or Anti-ACC from the clone of step (1); (3) Transforming the said antisense gene into the desired plant cells.

Cloning of the Pep or ACC Gene or a Fragment Thereof

The PEP or ACC gene of many crops have been reported, for example, in Yanai et al. Biosci Biotech Biochem, 58(5): 147~159. The said gene and fragment of the invention includes the full-length gene, the 3' or 5' UTR, or the introns or the coding sequences. The said gene and fragment of the present invention can be obtained by using the DNA synthesizer (American PE Inc.), or by PCR amplification. Preferred is the nest PCR. The primers for PCR are specifically designed for the target sequence of PEP or ACC of the selected oilseedcrops. The screening for the correct PCR product was accomplished through subcloning, electrophoresis and sequencing, all being well known by the skilled in the art. It can also be seen in, for example, *Molecular Cloning: A Laboratory Mannual*, Sambrook T, TanaKa K, Monma T. Cold Spring Harbor Laboratory après, New York, 1989.

Construction of the Antigenes Anti-PEP or Anti-ACC

The target PEP or ACC sequence was cut out from the subclone and recovered via electrophoresis. Next, the recovered sequence was ligated into the super-binary vectors, e.g., the plasmid pIG121 or pBI121, producing the transforming plasmid. Then, the said plasmids were transformed into the competent cells, e.g., the cells of *E. coli* HB101, which were later subjected to the resistance screen. All the operations were carried out according the standard methods, for example, in *Molecular Cloning: A Laboratory Mannual*, Sambrook T, TanaKa K, Monma T. Cold Spring Harbor Laboratory après, New York, 1989.

Plant Transformation and Regeneration

The transformation in the present invention was carried out via the techniques well known in the phyto-transgenics, including, but not limited to, *Agrobacterium* mediated transformation, microparticle bombardment and pollen tube process. Preferred was the *Agrobacterium* mediated transformation, which was detailed in, for example, *Molecular Cloning: A Laboratory Mannual*, Sambrook T, TanaKa K, Monma T. Cold Spring Harbor Laboratory après, New York, 1989. Then, normal plantlets could be regenerated through the co-cultivation of the hypocotyls with the *Agrobacterium tumefaciens*.

Identification of the Transgenic Rapeseed Plants

PCR analysis: Genome DNAs of a regenerated plant were extracted, and used as the templates in the PCR using the 5' and 3' primers of GUS gene (See examples thereinafter).

Southern blot analysis: Genome DNAs of the regenerated plants were completely digested with EcoRI. restriction enzyme, then, subjected to Southern blotting. The DNA fragment in the said super-binary vector comprising only the coding sequence for GUS gene was used as the probe, and labeled with $^{32}P$ using the Random Primer Labeling Kit from TaKaRa according to the instruction by the manufacturer.

GUS activity Assay: The said assay was carried out as described by Jefferson et al., in *Assaying Chimeric Genes in Plants: the GUS Gene Fusion System*. Plant Mol. Rep., Jefferson R A., 1987, 5: 387~405.

According to the present invention, the activity of the key enzyme in the protein biosynthesis or the limiting enzyme in the fatty acid biosynthesis was altered. Consequently, the flow direction of PEP, the common substrate for both protein and lipid biosyntheses, was controlled, which in turn desirably altered the ratio of proteins/lipids. For example, according to the present invention, when an antigene of PEP (the anti-PEP gene) was constructed and introduced into the desired plant cells, the activity of endogenous PEPCase was inhibited and the activity of ACCase was relatively increased. This led to more PEP flowing into fatty acid biosynthesis, finally, resulted in the seeds with significantly increased lipid content. As indicated, the present invention provides a novel desirably directed breeding method, successfully eliminating the drawbacks in the conventional breeding, such as randomness and time-consuming. In addition, it is advantageous over the known positive regulation approach by avoiding the technical difficulties, the complicated expression patterns of the target genes and the poor balance among the desired properties.

EXAMPLES

The present invention will now be further illustrated by taking the construction of the transgenic rapeseed with high lipid content for example. The other aspects, advantages and features will be apparent to one ordinary skilled in the art by reading the following examples with reference to the drawings. However, it should be noted that the examples are only given for the purpose of illustration, and are by no means intended to limit the scope of the invention that should only be defined by the appended claims.

Materials

Plant Materials: Zheyou758 (*Brassica napus* L.) and Zheyouyou No. 1, obtained from Institute of Crops, Zhejiang Academy of Agricultural Sciences were used.

Strains and plasmids: *E. coli* HB101(TaKaRa Company), *E. coli* JM109(TaKaRa Company), *A. tumefaciens* EHA101 (TaKaRa Company), plasmid pBS SK⁺ (ToYoBo Company), super-binary vector pIG121 (See, Yukoh Hiei, Shozo Ohta, Toshihiko Komari and Takashi Kumashiro. "Efficient transformation of rice (*oryza sativa* L.) mediated by *Agrobacterium* and sequence analysis of the boundaries of the T-DNA". The Plant Journal, 1994, 6(2).271–282) and pBI121(TaKaRa Company).

Enzymes and chemicals: The restriction-endonucleases, calf intestine alkaline phosphatase (CIAP), and T4-DNA ligase were purchased from MBI Company; Taq DNA Polymerase, from Sangon Biotechnical Company; the DNA Mark λ DNA/Hind III, from Huamei Biotechnical Company; DL2000, from TaKaRa Company; X-gal, IPTG and X-glue, from Sigma Chemical Company; the Random Primer Labeling Kit from TaKaRa Biotechnology Company, and the [α-$^{32}$P] dCTP, from Yahei Biotechnical Company. The primers used for PCR were synthesized by Sangon Biotechnical Company.

1. Cloning of PEP Gene Fragment

Two sets of primers were designed for the sequence of rapeseed PEP gene as reported by Yanai et al (Biosci Biotech Biochem, 58(5):147~159):

Primer1 (5'-primer): 5'-GGAATCTAAAGTAAAC-CGGC-3'(20-mer) (SEQ ID NO:1)

Primer2 (5'-primer): 5'-CTCTCTGAATCCTTCTGTAG-3'(20-mer) (SEQ ID NO:2)

Primer3 (3'-primer): 5'-AACCGACGGCCGTGACT-GTA-3'(20-mer) (SEQ ID NO:3).

Nest PCR was carried out using a Perkin Elmer Gene Amp PCR System 9600 according to instruction by the manufacturer.

A 610 bp DNA fragment was first obtained using the outside primer pair (primer 1 and primer 3). This 610 bp fragment was used as template for the second round of PCR with the inside primer pair (primer2 and primer3). A 530 bp fragment was thus obtained with the right length as expected. The 3'-end of the 530 bp fragment was made blunt through a filling-in using the T4 DNA polymerase. The blunt ended fragment was then subcloned into the vector pBS SK$^+$, which was then transformed into the competent cells of E. coli JM109. The recombinants was selected by growing on the selective plate containing Amp, X-gal and IPTG at 37° C. over night, and picking the white clones. Plasmids were extracted, then subjected to EcoRI/BamHI digestion followed by electrophoresis. The plasmids of correct size were sequenced with the Sangar terminal termination method using the DNA Sequencer model 370 from MBI Company. One recombinant was identified having the insert with 100% homology to the sequence of rapeseed PEP gene as reported. This recombinant was designated as pPEP8, and used in the further process.

Figure 1:
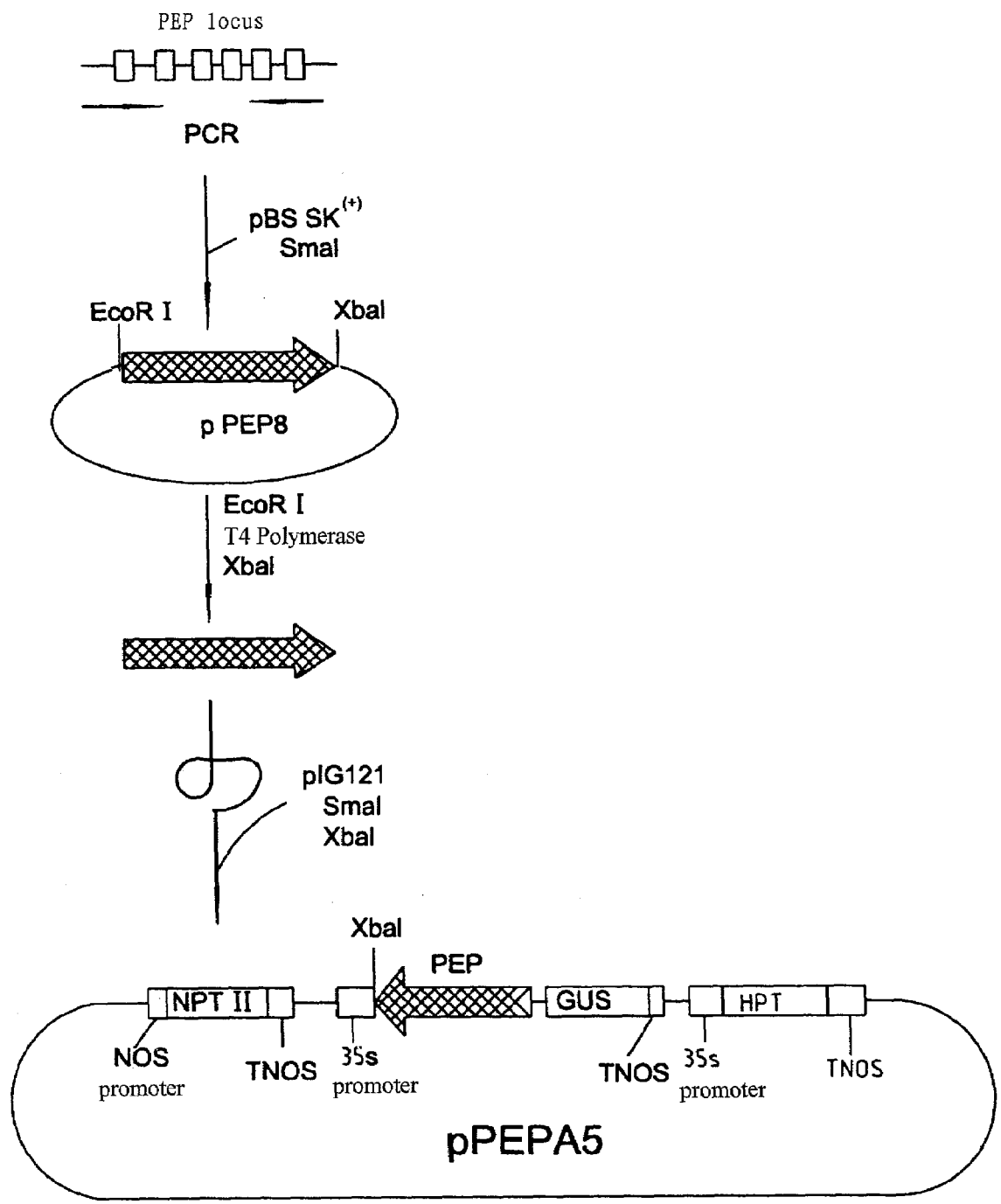
FIG. 1 shows the strategy of construction of the recombinant plasmid pPEPA5.

2. Construction of the Constructure as Anti-PEP Gene/Super-Binary Vector 2.1 Strategy for Constructing the Constructure as Anti-PEP Gene/pIG121 Super-Binary Vector Reference was made to FIG. 1. The Xba1 site was used for orientation. The PEP fragment was released from the pPEP8 with the EcoRI restriction enzyme. The 5' end of the obtained restriction fragment was blunted by filling-in using T4-DNA polymerase. Then, the 3' end of the said fragment was cleaved by the Xba1 enzyme. The resulted restriction fragment was recovered via low melting point agarose electrophoresis. Separately, the plasmid pIG121 was cleaved with the SmaI enzyme to create a blunt 5' end, and the 3' end, with the Xba1 enzyme. The two fragments, i.e., the restriction PEP fragment from the pPEP8 and the restriction opened vector pIG121 were ligated together using the T4-DNA ligase. Consequently, recombinant plasmid pPEPA5 was obtained, wherein, the said PEP fragment was inserted downstream of the 35S promoter of CaMV and upstream of the GUS reporter gene, and was inversely linked to the 35S promoter.

2.2 Strategy for Constructing the Anti-PEP/pBI121 Binary Vector

Figure 2:
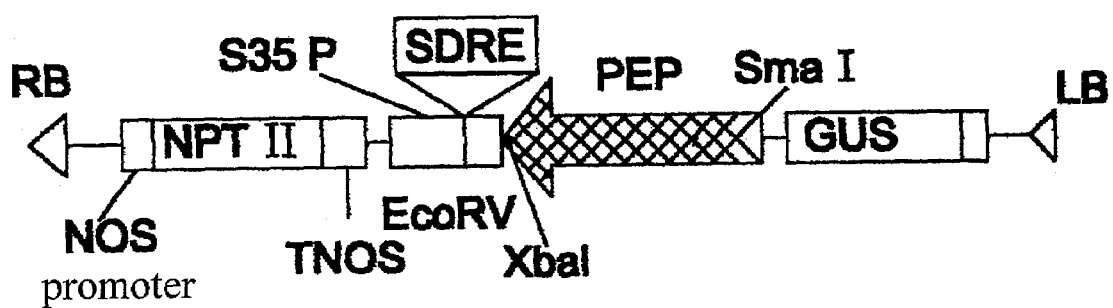
FIG. 2 shows the strategy of construction of the recombinant plasmid Anti-PEP/pBI121, i.e. pPEPA5'.

Reference was made to FIG. 2. Anti-PEP/pBI121 binary vector was constructed by the procedure as described in the above section 2.2, except that the vector pBI121 was used instead of pIG121. the recombinant plasmid pPEPA5' was thus produced (anti-PEP/pBI121). The pBI121 binary vector contained the GUS gene under the control of the 35S promoter and NPTII gene under the NOS promoter, as well as the SERE element controlling the specialization and development of the seeds.

3. *A. tumefaciens* Mediated Transformation

Figure 3:
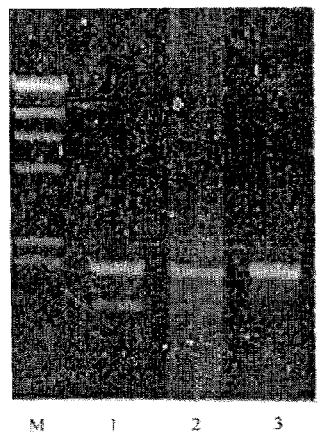
FIG. 3 shows the electrophoresis patterns of the PCR products of plasmids pPEPA5, *E. coli*HB101/pPEPA5 and *Agrobacterium tumefaciens* EHA101/pPEPA5, wherein, M: DNA Mark λ DNA/Hind III; lane 1: PCR product of pPEPA5; lane 2: PCR product of *E. coli* HB101/pPEPA5; lane 3: PCR product of *Agrobacterium tumefaciens* EHA101/pPEPA5.

The recombinant plasmid obtained in section 2.1 or 2.2 was transformed into the competent cells of *E. coli* HB101. The positive recombinants were selected. The plasmids therein were extracted using the alkaline process, and identified via restriction cleavage. The recovered constructure, Anti-PEP gene/super binary vector, i.e., pPEPA5 or pPEPA5', was transferred into the *Agrobacterium* strain EHA101 by, for example, electroporation, producing the EHA101/pPEPA5(or EHA101/pPEPA5'), see FIG. 3.

4. Plant Transformation and Regeneration

The vector pIG121 contained the GUS reporter gene and the hygromycin resistance marker under the 35S promoter, and the NPT II gene under the NOS promoter. Therefore, the transgenic rapeseed plants could be screened for the hygromycin-resistance, and the integrity of the exogeneous gene could be determined through the expression of the GUS gene. Sterile hypocotyls from those 8~10 days old seedlings were cut and used as recipient in the transformation with the anti-PEP gene. The *A. tumefaciens* EHA10/pPEPA5 were used to infect the hypocotyl explants. After a 2 days co-cultivation, the hypocotyl explants infected with *A. tumefaciens* EHA101/pPEPA5 were transferred to the MS medium containing 500 mg/L carbenicillin (Cb). An additional week later, they were transferred to the MS differentiation medium containing 500 mg/L carbenicillin and 10 mg/L hygromycin, in order to effect the resistance selection.

Figure 4:
FIG. 4 shows the process of regeneration of the transformed rapeseed plants.

Callus growth occurred at the cut ends of the hypocotyls in the following 3~4 weeks. Gradually, appeared the green resistant shoots and the white non-resistant shoots. The green shoots, when reaching at least 1 cm tall, were cut at the base and transferred to the root-inducing medium containing the same antibiotics. Two weeks later, the said green shoots rooted and grew into intact mini-plants. The mini-plants were transferred to the soil, and grown into normal plants. The plants grew and developed until seeds were produced and harvested. See FIG. 4.

For 2 consecutive years, we have succeeded in introducing via *Agrobacterium* mediated transformation the anti-PEP gene into the genomes of rapeseeds, specifically, Zheyou 758 and Zheyouyou No. 1. Also, we have thus successfully obtained several batches of transgenic plants with optimized reproducibility, and established a high efficient transgenic rapeseed system.

Identification of Anti-PEP transgenic rapeseed

PCR analysis: The integration of exogenous gene into the genomes of the transformed plants can be rapidly identified by PCR. Since the rapeseeds contain endogenous PEP gene, the DNA sequence of PEP gene itself can not be contained in the primers and the probes for identification by PCR and southern blotting. In the present invention, the following primers flanking the GUS gene were used for PCR amplification.

Primer4(5'-primer) 5'-CGTAAGGGATGACGCACAAT-3' (20-mer) (SEQ ID NO:4), Primer5(3'-primer) 5'-CGCAAGACCGGCAACAGG-3' (18-mer) (SEQ ID NO:5).

Figure 5:
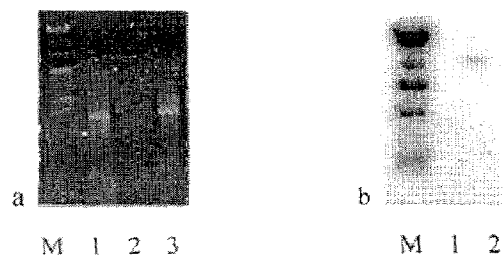
FIG. 5 shows the results of identification of the transgenic rapeseed plants.
Figure 5:
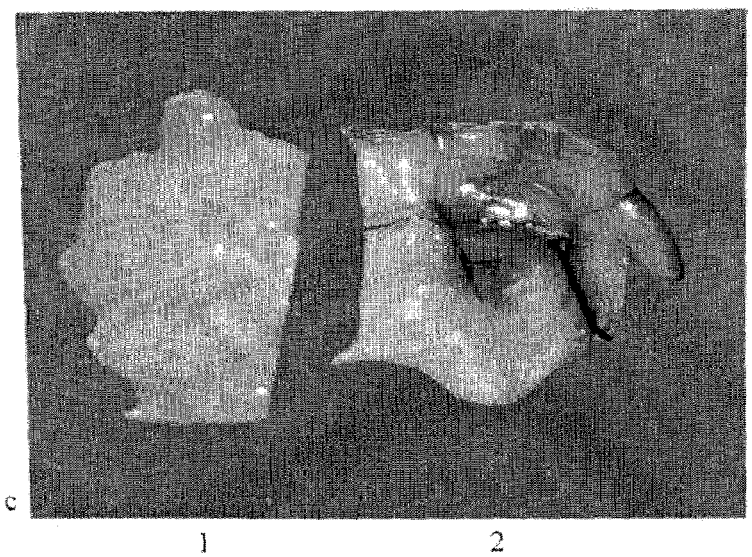

The genome DNAs of the regenerated plants were extracted and used as templates in the PCR amplification. For the transgenic plant, a band of Mw corresponding to the recombinant pPEPA5 containing the anti-PEP gene was obtained. However, such band was not observed for the control (FIG. 5a).

Southern analysis: The genome DNAs of the regenerated plants were completely digested with the EcoRI enzyme. The digestion product was then subjected to the Southern blotting. The DNA probe was a 2.0 kb Sal I fragment derived from the super-binary vector pIG121. The said fragment contained only the GUS gene. The probe was labeled using the Random Primer Labeling Kit from TaKaRa according to the instruction by the manufacturer. This probe was observed hybridizing with the DNA of the regenerated transgenic plant, producing a hybrid band of ~8.8 Kb. (FIG. 5b).

Assay of GUS activity: The said assay was carried out as described by Jefferson et al., in Assaying Chimeric Genes in Plants: the GUS Gene Fusion System. Plant Mol. Rep., Jefferson R A., 1987,5: 387–405).

The leaves and root tips of the transgenic plants were used for GUS histochemisty assay. GUS blue reaction was observed for the leaves and root tips of the transgenic plants, but not for the control. (FIG. 5c).

uct Quality Monitoring Validation Center, the lipid content of the transgenic rapeseeds of the invention can reach as high as 47.48%, almost 25.0% higher than that of the control. (FIG. 6).

The protein and lipid contents in Zheyouyou No. 1 were assessed according to the Kjeldahl's method (Zhang Longxiang, Zhang Tingfang, Li Lingyuan. Methods and Technology of Biochemistry. Beijing: Higher Education Press.). The seeds of the 9 transgenic rapeseed plants of the T1 generation and the seeds of the parent plants as control were used in the assay. The assessment was done by Department of Agriculture, Oil and Product Quality Monitoring Validation Center. The results are summarized in tablet 1. The average contents of protein and lipid in the transgenic plants were 48.63%±1% and 22.80%±0.64%, respectively, while those of the controls were 41.67%±0.95% and 24.11%±0.08%, respectively. The value of the trasgenic plants was 16.7% higher than the control on average. One transgenic plant had a value of 49.54%, 18.89% higher than the control. The correlation between the protein content (Y) and the lipid content (X) could be expressed by formula: $y=32.36-0.2x$. The correlation coefficient "r" was 0.82. The above results indicated that the protein and the lipid contents in the crop seeds were significantly inversely correlated to each other. As measured by the Zhejiang Province Grain and Lipid Product Quality Monitoring Institute, the lipid content in the transgenic plants could be as high as 52.7%, 25.5% higher than that of the control. (FIG. 7).

TABLE 1

Protein and lipid contents in the transgenic Zheyouyou No. 1

| Zheyouyou No. 1 | Transgenic Plants | | | | | | | | | Non-transgenic plants | | | |
|---|---|---|---|---|---|---|---|---|---|---|---|---|---|
| Lipid Content (%) | 48.69 | 49.42 | 47.04 | 47.60 | 49.44 | 49.40 | 49.54 | 47.18 | 49.38 | 42.6 | 42.62 | 40.68 | 40.76 |
| Protein Content (%) | 22.50 | 22.24 | 23.66 | 22.52 | 22.68 | 22.86 | 23.04 | 23.94 | 21.77 | 24 | 24.22 | 24.14 | 24.06 |

Note:
The assessment was done by the Department of Agriculture, Lipid and Product Quality Monitoring Validation Center.

The above result indicated that the exogenous gene had been integrated into the genome of the rapeseed and stably expressed. Since the anti-PEP gene was inserted between the 35S promoter and GUS gene, the above results indicated that the anti-PEP gene had been introduced into the rapeseed genome and stably expressed.

6. Assessment of the Protein and Lipid Contents in the Transgenic Rapeseed Seeds The lipid content in Zheyou 758 was assessed. The assessment was accomplished by the Zhejiang Province Grain and Lipid Product Quantity Monitoring Institute. For 4 independent transgenic plants of the T1 generation, the average oil content in the seeds was 32.83±2.63%, while the value for the controls was 30.83±1.91%. The said value of the transgenic plant was 6.4% higher than that of the control on average. One transgenic plant had a lipid content of 35.50%, 15.15% higher than that of the control.

The lipid contents in 50 Zheyou 758 plants of T2 generation were assessed, and scored as high, mediate and low. The distribution of plants scored as high, mediate and low was 8:29:13, well conforming to the Mendelian 1:2:1 segregation ratio of a single gene controlled character. As determined by the Department of Agriculture, Oil and Prod- 7. SDS-PAGE Electrophoresis of Proteins in Seeds of the Transgenic Rapeseed (1) Preparation of samples: The seeds were pulverized, 100 mg was weighted and added into 100 µl extracting solution (containing 1% SDS, 5% β-mercaptoethanol in water). After a 10 min extraction, the cell debris were removed by centrifugation at 10,000 rpm for 15 min. The resulted supernatants were separated, to which was added the equal volume of the sample solution (containing 4% SDS, 10% β-mercaptoethanol, 20% glycerol, 0.01% bromophenol blue and 0.004M, pH6.8, Tris-HCl). The mixture was incubated at 100° C. for 1 min. (2) Electrophoresis: This was carried out on a 10% separating gels, as described, for example, by Zhu Guanglian and Yangzhonghan in *Detection of molecular weight of proteins by SDS-PAGE electrophosphate*. Plant Physiology Communications.

The SDS-PAGE results indicated that there were no significant differences between the transgenic plants and the control, in qualities and identities of the storage proteins in the seeds. However, corresponding to the different total proteins amount in the seeds, the densities of the bands of main storage proteins were significantly varied. Meanwhile, no such variation was observed for other proteins. (FIG. 8).

8. The RAPD analysis of the transgenic rapeseeds

The genome DNAs of Zheyouyou No. 1/anti-PEP and Zheyouyou No. 1 plants as control were extracted according to the CTAB method, and diluted into 20 ng/μl (Wang Guanlin, Fan Hongjuin. Principle and Technology of Plant Genetic Engineering, Beijing: Science & Technology Press). PCR was done in a volume of 25 μl. The random 10-mer primers were prepared by Sangon Biotechnical Company. The following 40 primers were used:

| S1 | GTTTCGCTCC | (SEQ ID NO:6) |
|---|---|---|
| S2 | TGATCCCTGG | (SEQ ID NO:7) |
| S3 | CATCCCCCTG | (SEQ ID NO:8) |
| S4 | GGACTGGAGT | (SEQ ID NO:9) |
| S5 | TGCGCCCTTC | (SEQ ID NO:10) |
| S6 | TGCTCTGCCC | (SEQ ID NO:11) |
| S7 | GGTGACGCAG | (SEQ ID NO:12) |
| S8 | GTCCACACGG | (SEQ ID NO:13) |
| S9 | TGGGGGACTC | (SEQ ID NO:14) |
| S10 | CTGCTGGGAC | (SEQ ID NO:15) |
| S11 | GTAGACCCGT | (SEQ ID NO:16) |
| S12 | CCTTGACGCA | (SEQ ID NO:17) |
| S13 | TTCCCCCGCT | (SEQ ID NO:18) |
| S14 | TCCGCTCTGG | (SEQ ID NO:19) |
| S15 | GGAGGGTGTT | (SEQ ID NO:20) |
| S16 | TTTGCCCGGA | (SEQ ID NO:21) |
| S17 | AGGGAACGAG | (SEQ ID NO:22) |
| S18 | CCACAGCAGT | (SEQ ID NO:23) |
| S19 | ACCCCCGAAG | (SEQ ID NO:24) |
| S20 | GGACCCTTAC | (SEQ ID NO:25) |
| S21 | CAGGCCCTTC | (SEQ ID NO:26) |
| S22 | TGCCGAGCTG | (SEQ ID NO:27) |
| S23 | AGTCAGCCAC | (SEQ ID NO:28) |
| S24 | AATCGGGCTG | (SEQ ID NO:29) |
| S25 | AGGGGTCTTG | (SEQ ID NO:30) |
| S28 | GTGACGTAGG | (SEQ ID NO:31) |
| S29 | GGGTAACGCC | (SEQ ID NO:32) |
| S82 | GGCACTGAGG | (SEQ ID NO:33) |
| S106 | ACGCATCGCA | (SEQ ID NO:34) |
| S112 | ACGCGCATGT | (SEQ ID NO:35) |
| S134 | TGCTGCAGGT | (SEQ ID NO:36) |
| S211 | TTCCCCGCGA | (SEQ ID NO:37) |
| S271 | CTGATGCGTG | (SEQ ID NO:38) |
| S293 | GGGTCTCGGT | (SEQ ID NO:39) |
| S362 | GTCTCCGCAA | (SEQ ID NO:40) |
| S386 | GAGGGAAGAG | (SEQ ID NO:41) |
| S425 | ACTGAACGCC | (SEQ ID NO:42) |
| S440 | GGTGCTCCGT | (SEQ ID NO:43) |
| S469 | GTGGTCCGCA | (SEQ ID NO:44) |
| S1117 | GCTAACGTCC | (SEQ ID NO:45) |

The buffer solution used was the PCR buffer from MBI Company. Each reaction system comprised: 10 mM Tris HCl (pH 8.3), 2.0 mM MgCl, 50 mM KCl, 0.8% Nonidet P40, 200 uM each of dATP, dCTP, dGTP and dTTP, 0.15 μM each of the 10mer primers, 1 unit Taq DNA polymerase (MBI Company) and 20 ng DNA template. The Amplification was performed on the Perkin Elmer Gene Amp PCR System 9600. The PCR procedure was: 95° C. predenaturing, 5 min; 94° C., 1 min, 37° C., 2 min and 72° C., 1 min, totally 45 cycles; finally, 72° C. extension, 10 min. 15 μl PCR product was used in a 1.5% agarose gel electrophoresis. Photographs were taken under UV lamp after stained with ethidium bromide.

Primers S9 and S106 failed in the PCR with no product obtained. The other 38 primers produced totally 197 DNA bands, having sizes ranging from 0.1 to 4.0 kb. For the 38 primers, the PCR product bands for two templates were almost the same (FIGS. 9 and 10), except that primer S271(No. 11 and 12 in FIG. 9) produced 8 bands derived from Zheyouyou No. 1/anti-PEP including one special band of 560 bp. This 560 bp band was not found in products of the control as Zheyouyou No. 1 (FIG. 9, FIG. 10). It is obvious that the differences between the genomes of Zheyouyou No. 1/anti-PEP and Zheyouyou No. 1 were minimal.

9. Ultra-Microscopic Examination of the Lipids and Proteins in the Storage Cells of the Transgenic Rapeseed Seeds In the storage cells of the transgenic rapeseed seeds, the lipid bodies were in the shape of polygons, and were tightly arranged in the mosaic pattern, barely having any gaps between them. The lipid bodies along the cell wall were in the shapes of longitude or polygon. (FIG. 11a). On the other hand, in the control, the lipid bodies were in the shape of ellipses, and were loosely dispersed in the cells, having large gaps between them. (FIG. 1b).

10. Effects of Anti-PEP on Other Oil Crops

The antisense oligonucleotide of PEP was also introduced into sunflowers (G101 line) and sesames using the ASODN method (Cheng Zhongbin et al. 1999, Effects of chemical modifications on the stability of the antisense and activity of the antiinfluenza virus, Chinese Journal of Biochemistry and Molecular Biology. 15,(4):605~609; CHENG, Jiannan et al. 1998; The relationship between the cytoplasmic male sterile of sorghum and $HSC_{70}$ mRNA. Science Bulletin. 43(23): 2525~2530).

Antisense oligonucleotide of PEP was synthesized. Three nucleotides at either of the 5' and 3' ends were phosphorothioated to inhibit the degradation by the endogenous Rnase in the plants. The sequence was: 5'-$gx_1g$ $gx_1g$ $gx_2a$ $cx_1g$ $tx_3g$ $gx_4a$ gag gag $gx_5g$ $gx_6c$ $cx_7$-3' (SEQ ID NO:46). Wherein, $x_1$=t or a; $x_2$=c or g; $X_3$=C or t or g; $x_4$=a or g; $x_5$=t or c, $x_6$=t or g; $x_7$=a or c or g.

The synthesized antisense oligonucleotide of PEP was terminally labeled with [$\lambda$-$^{32}$P]. The [$\lambda$-$^{32}$P] dATPs were purchased from Yahui Biotechnical Company, T4-polynucleotode kinase was purchased from TaKaRa Company. The labeling was carried out according to the instruction by the manufacturer. The purification of the [$\lambda$-$^{32}$P] labeled antisense oligonucleotide was carried out as described by Sambrook T, TanaKa K, Monma T. In *Molecular Cloning: A Laboratory Mannual*, Cold Spring Harbor Laboratory après, New York, 1989.

The transportation of the antisense oligonucleotide of PEP in the plant was examined. At 8:00 am, 5 μl labeled antisense oligonucleotide of PEP was injected into the branch beneath the young beanpods using a 5-guage needle through a hole into the center of the stem. At 4:00 pm, the stem was cut down for the autoradiography after counting the young beanpods on the branch. The oil contents of the matured seeds were measured using the Soxhlet method. The results were shown in FIG. 12 and FIG. 13, indicating an average increase in the oil contents of 6.32% over the controls in sunflowers and 8.63% in sesames.

The present examples along with the methods, procedures, treatments, molecules and specific compounds described herein are presently representative of the preferred embodiments, and by no means limit the scope of the invention. Changes therein and other uses will occur to those skilled in the art which are encompassed within the spirit and scope of the invention as defined by the claims.

The invention claimed is:

1. A method for increasing the ratio of lipids to proteins in oilseed crop seeds, comprising:
   (1) Cloning DNA encoding phosphoenolpyruvate carboxylase (PEPCase) or a PEPCase fragment, wherein the DNA encoding PEPCase or the PEPCase fragment is selected from the group consisting of a full length of the DNA encoding PEPCase, a 3' or 5' UTR of the DNA, introns of the DNA, or coding sequences of the DNA;
   (2) Constructing an antigene (Anti-PEP) from the clone of step (1);
   (3) Transforming a desired plant with a construct consisting essentially of:
      (i) the Anti-PEP;
      (ii) at least one regulatory sequence; and
      (iii) a selectable marker;
   (4) Regenerating the transformed plant; and
   (5) Harvesting oilseed crop seeds comprising an increased ratio of lipids to proteins.

2. The method according to claim 1, wherein the PEPCase fragment comprises 100–500 bps.

3. The method according to claim 1, wherein the cloning the DNA encoding PEPCase comprises:
   obtaining the DNA encoding PEPCase or the PEPCase fragment through PCR amplification or artificial synthesis;
   selecting recombinants by sub-cloning and transformation; and
   identifying the insert by restriction digesting, electrophoresis and DNA sequencing.

4. The method according to claim 3, wherein the PCR is nest PCR.

5. The method according to claim 1, wherein constructing the Anti-PEP comprises:
   cutting out the cloned gene or fragment with restriction enzymes, whereby a restriction fragment is produced;
   recovering the restriction fragment through electrophoresis; and
   ligating the restriction fragment into a super-binary vector.

6. The method according to claim 1, wherein the transformation is effected by the means selected from the group consisting of *Agrobacterium tumefaciens* mediated transformation, particle bombardment or pollen tube mediated transformation.

7. The method according to claim 1, wherein the plant is selected from the group consisting of soybean, rapeseed, peanut, sunflower or sesame.

8. A plant produced by the method of claim 1, containing the Anti-PEP.

9. A method for increasing the ratio of lipids to proteins in crop seeds, comprising:

obtaining DNA encoding phosphoenolpyruvate carboxylase ("PEPCase") or a PEPCase fragment, wherein the DNA encoding PEPCase or the PEPCase fragment is selected from the group consisting of a full length of the DNA encoding PEPCase, a 3' or 5' UTR of the DNA, introns of the DNA, or coding sequences of the DNA;

constructing an Anti-PEP antigene from the DNA encoding PEPCase or the PEPCase fragment;

integrating into a desired plant genome a construct consisting essentially of:
   (a) the Anti-PEP antigene;
   (b) at least one regulatory sequence; and
   (c) a selectable marker;

regenerating the transformed plant; and selecting seeds from the transformed plant comprising an increased ratio of lipids to proteins.

* * * * *

UNITED STATES PATENT AND TRADEMARK OFFICE
CERTIFICATE OF CORRECTION

PATENT NO. : 7,176,350 B2
APPLICATION NO. : 10/142111
DATED : February 13, 2007
INVENTOR(S) : Jinqing Chen et al.

It is certified that error appears in the above-identified patent and that said Letters Patent is hereby corrected as shown below:

Title page, Item (75), " Zhanghu " should read -- Zhanghua --

Title page, Item (75), " Xhihong " should read -- Zhihong --

Signed and Sealed this

Eighth Day of May, 2007

JON W. DUDAS
*Director of the United States Patent and Trademark Office*